United States Patent
Lee

Patent Number: 5,867,610
Date of Patent: *Feb. 2, 1999

[54] METHOD FOR IDENTIFYING OBJECTS USING DATA PROCESSING TECHNIQUES

[75] Inventor: Shih-Jong J. Lee, Bellevue, Wash.

[73] Assignee: NeoPath, Inc., Redmond, Wash.

[*] Notice: The term of this patent shall not extend beyond the expiration date of Pat. No. 5,710,842.

[21] Appl. No.: 904,971

[22] Filed: Aug. 1, 1997

Related U.S. Application Data

[62] Division of Ser. No. 615,468, Mar. 14, 1996, Pat. No. 5,710,842, which is a division of Ser. No. 179,812, Jan. 10, 1994, Pat. No. 5,528,703, which is a continuation-in-part of Ser. No. 838,395, Feb. 18, 1992, abandoned.

[51] Int. Cl.$^6$ ..................................................... G06K 9/36
[52] U.S. Cl. ........................... 382/283; 382/213; 382/257
[58] Field of Search .................................... 382/283, 254, 382/257, 213; 324/309, 307; 358/456

[56] References Cited

U.S. PATENT DOCUMENTS

| | | | |
|---|---|---|---|
| 5,131,049 | 7/1992 | Bloomberg et al. | 382/257 |
| 5,204,627 | 4/1993 | Mistretta et al. | 324/309 |
| 5,710,842 | 1/1998 | Lee | 382/283 |

*Primary Examiner*—Jose L. Couso
*Assistant Examiner*—Anh Hong Do
*Attorney, Agent, or Firm*—Hans I. Sun; Emil Moffa

[57] ABSTRACT

A method for identifying the size, shape, and location of objects in a specimen where the image of the specimen is represented by image data and where the image data is processed to provide mask data representing a mask where the mask identifies the size, shape, and location of the object. Generally, the method includes the step of enhancing the image and creating a threshold image where the threshold image includes a threshold intensity value associated with each pixel of the image. The threshold image is combined with the original image to provide a mask image that identifies the size, shape, and location of the objects. The mask image may be further refined to ensure accurate identification of the object. Various other techniques are disclosed within the general method for processing image data.

9 Claims, 12 Drawing Sheets

METHOD FOR IDENTIFYING OBJECTS USING DATA PROCESSING TECHNIQUES

RELATED APPLICATIONS

This application is a division of application Ser. No. 08/615,468, filed Mar. 14, 1996, U.S. Pat. No. 5,710,842, which is a divisional of pending application Ser. No. 08/179,812, U.S. Pat. No. 5,528,703, filed Jan. 10, 1994, which is a continuation-in-part of application Ser. No. 07/838,395, filed Feb. 18, 1992, abandoned.

TECHNICAL FIELD

The present invention is directed toward a method for identifying objects using data processing techniques and, more particularly, toward a method for use in combination with image analysis apparatus for identifying objects of interest within the field of view of an image analysis microscope.

BACKGROUND OF THE INVENTION

With increasing progress in data processing technology, both hardware and software, biomedical analysis systems are becoming more and more prevalent. Presently, image enhancement systems have been developed for providing images of body systems such as, for example, magnetic resonance imaging devices, ultrasound imaging, computer tomography imaging, etc. Image enhancement systems are typically used for capturing and processing data to be used to provide an image of functional systems of a patient, as for example, the patient's heart, lungs, etc. These systems make no attempt to collect or analyze other data representing the functional systems of the patient.

Other image analysis systems have been developed that are used for analyzing image data of specimens taken from a patient. As examples, devices have been provided for analyzing image data representing blood cells, bone marrow cells, brain cells, etc. Image analysis systems are typically designed to capture and process image data to be used to determine characteristics of the specimen, as for example, blood cell count. These systems attempt to identify various objects within the specimen, e.g., individual cells, so that the characteristics of the object can be further analyzed to determine the overall quality or condition of the specimen. However, prior image analysis systems have failed to provide effective methods or apparatus for identifying individual objects of interest within the specimen without special preparation of the specimen.

As an example, image analysis systems have been provided to screen portions of a cervical Pap smear. These systems typically require special preparation for the cervical Pap smear specimen before the specimen can be examined. This is because a typical cervical Pap smear specimen, that may be examined by a cytotech without the aid of an image analysis system, includes layers and chunks of cells that cannot readily be identified using available imaging data processing technology. However, the special preparation required for these analysis systems require additional steps in the preparation of the specimen and, therefore, increase the overall expense and complication of the analysis.

Accordingly, it is desirable to provide a method for identifying objects of interest within the field of view of a microscope of an image analysis system without requiring special preparation of the specimen being imaged. Further, it is desirable to provide a method for identifying objects of interest within the field of view of a microscope of an image analysis system that is capable of identifying individual objects that may be located proximate other objects. More particularly, it is desirable to provide a method for use with image analysis systems for identifying cells of a cervical Pap smear specimen.

SUMMARY OF THE INVENTION

The subject invention provides a method for creating a mask to identify objects of interest wherein the objects of interest are contained in an image represented by an array of image data. The method includes the steps of processing the data representing the image to create a threshold image wherein the threshold image is an array of data words, each data word of the threshold image corresponding to a respective data word of the image. A binary image is created by comparing each data word of the threshold image with its respective data word of the image wherein the binary image is an array of data words each corresponding to a respective data word of the image and wherein each data word of the binary image identifies whether the respective data word of the image was greater than the respective data word of the threshold image. Holes are filled in the binary image by inverting the binary image and excluding data representing an object of size less than the expected size of the holes of the objects of interest by predetermined amount, the identified objects are then added back to the binary image to create a preliminary mask. The data representing the preliminary mask is processed to detect its dark edges and combined with the preliminary mask to create data representing a dark edge incorporated mask. The data representing the preliminary mask is also processed to detect its bright edges and combined with the dark edge incorporated mask to create data representing a mask identifying the objects of interest.

DETAILED DESCRIPTION OF THE INVENTION

Figure 1:
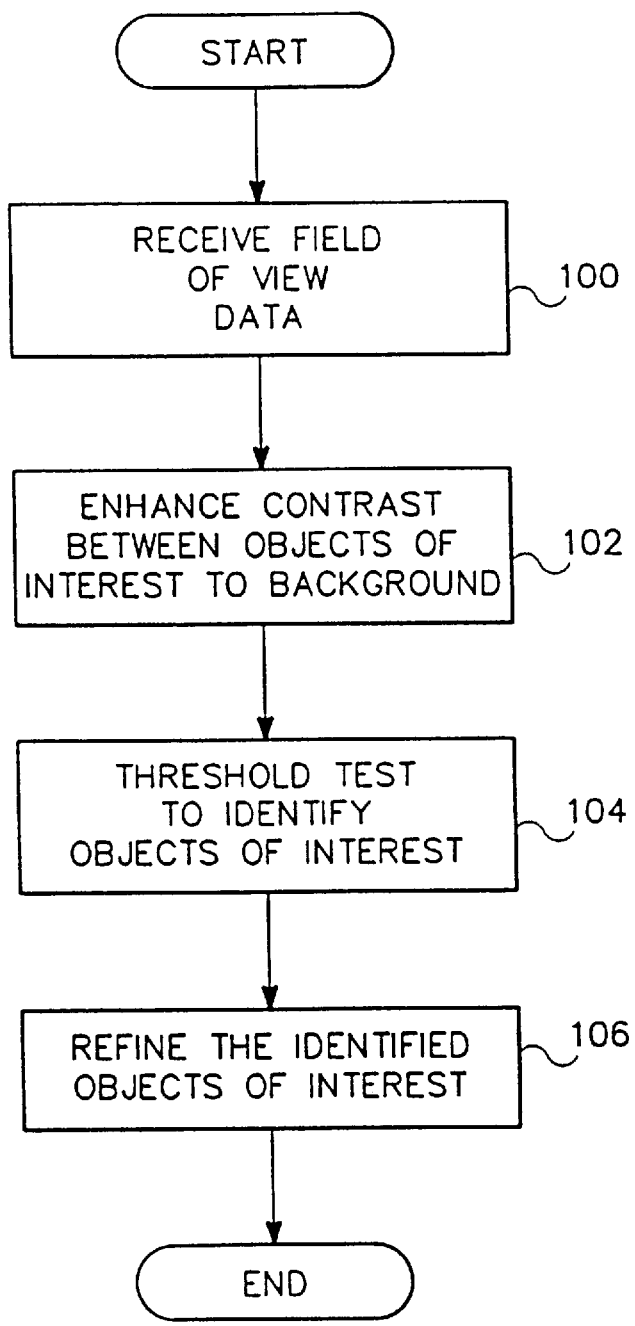
FIG. 1 is a method flow diagram illustrating generally the steps of the subject invention.

As mentioned above, the present invention comprises a method for use with image analysis systems for identifying objects of interest within the field of view of a microscope of the image analysis system. The method of the subject invention is particularly suited for use with image analysis systems constructed for analysis of cytological specimens and, more particularly, for analysis of the characteristics of the cells of the specimen. However, the subject invention is generally applicable to any system for processing image data and, therefore, could be readily adapted to be used in many areas of image analysis such as machine vision, semiconductor inspection, etc. Accordingly, although the subject invention is described herein by reference to an image analysis system constructed to analyze cervical Pap smears, those skilled in the art will recognize that the invention is applicable to many areas of image analysis.

An image analysis system typically includes a microscope, a camera, and data processing devices for providing data representing a field of view of the microscope. The field of view data is analyzed to identify the objects of interest and to characterize the objects of interest to determine whether the specimen on the slide is normal or abnormal. Suitable apparatus for obtaining the field of view data is shown and described in pending U.S. patent application Ser. No. 08/302,355, filed Sep. 7, 1994, allowed, which is a continuation-in-part of abandoned U.S. patent application Ser. No. 07/838,063, for Method and Apparatus for Rapid Capture of Focused Microscope Images, by Jon W. Hayenga et al., filed Feb. 18, 1992 and assigned to the present assignee, now abandoned, and U.S. Pat. No. 5,361,140 issued Nov. 1, 1994 entitled Method and Apparatus for Dynamic Correction of Microscope Image Signals, by Jon W. Hayenga et al., assigned to the present assignee, the disclosures of which are incorporated herein, in their entireties, by the foregoing references thereto. Suitable apparatus for analyzing the FOV data in accordance with the methods discussed herein is shown and described in U.S. Pat. No. 5,315,700 issued May 24, 1994 entitled Method and Apparatus for Rapidly Processing Data Sequences, by Richard S. Johnston et al., assigned to the present assignee, the disclosure of which is incorporated herein in its entirety, by the foregoing reference thereto.

It will be appreciated by those skilled in the art that the subject invention comprises a method for performing a necessary step in the overall analysis of cervical Pap smear specimens. Particularly, the subject method is provided for identifying objects of interest within the field of view of the microscope. Other methods must then be employed to analyze the characteristics of the identified objects of interest and determine the overall condition of the specimen. Suitable methods for performing this analysis are shown and described in U.S. Pat. No. 5,787,188, issued Jul. 28, 1998, which is a file wrapper continuation of abandoned U.S. Pat. No. 5,787,188, file wrapper continuation patent application Ser. No. 07/838,064, for Method for Identifying Normal Biomedical Specimens, by Alan C. Nelson et al., filed Feb. 18, 1992 and assigned to the present assignee, the disclosure of which is incorporated herein, in its entirety, by the foregoing reference thereto.

The subject method for identifying objects of interest within the field of view of a microscope is illustrated generally in FIG. 1. Therein, the first step is to receive the field of view data for analysis, step 100. The field of view data is data from the microscope of the image analysis system that represents the image of a field of view of the microscope. In a presently preferred embodiment of the invention, the microscope imaging apparatus may provide as many as 15,000 fields of view for one specimen. However, it will be apparent to those skilled in the art that many fields of view will have no objects of interest. Accordingly, the data received in step 100 is assumed to have been prescanned, or otherwise preselected, as field of view data that includes objects of interest. Suitable methods for preselecting field of view data is discussed in the above referenced U.S. Patent entitled Method for Identifying Normal Biomedical Specimens, by Nelson et al.

The field of view data is typically an array of data words wherein each data word represents a pixel (picture element) of the camera of the image analysis system. In the presently preferred embodiment of the invention, the field of view data is grayscale field of view data, i.e., each data word is a multiple bit binary data word wherein the value of the data word is indicative of the transmissivity of the portion of the specimen associated with the pixel represented by the data word. However, portions of the present invention are equally applicable to binary field of view data, i.e., data wherein each data word indicates either the presence or absence of an object in the portion of the specimen associated with the pixel represented by the data word.

Figure 2A:
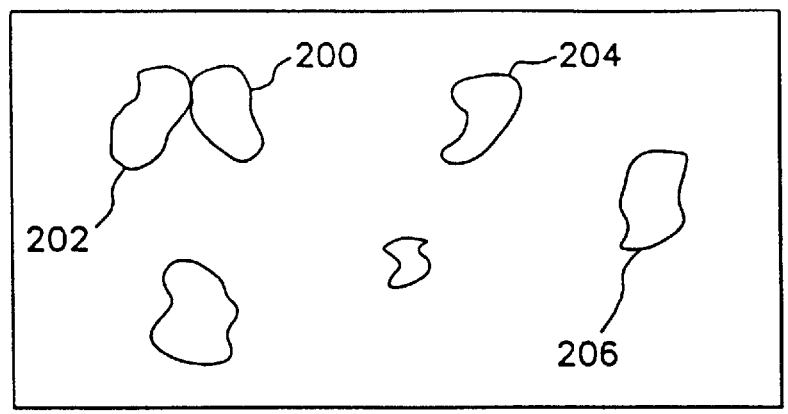
FIGS. 2A, 2B, and 2C are diagrams illustrating objects of a specimen on a slide.
Figure 2B:
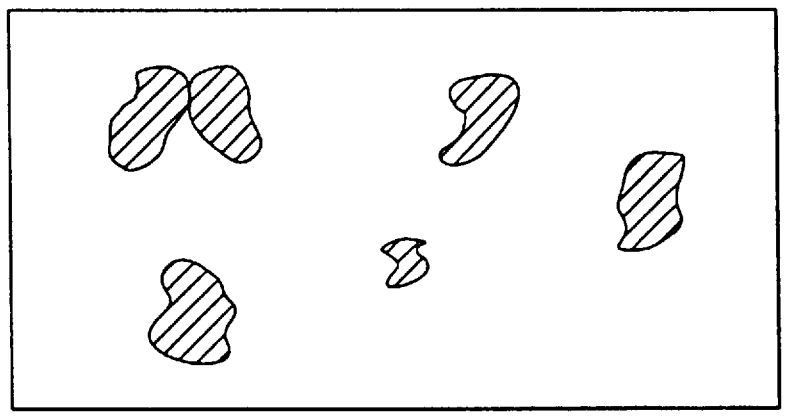
Figure 2C:
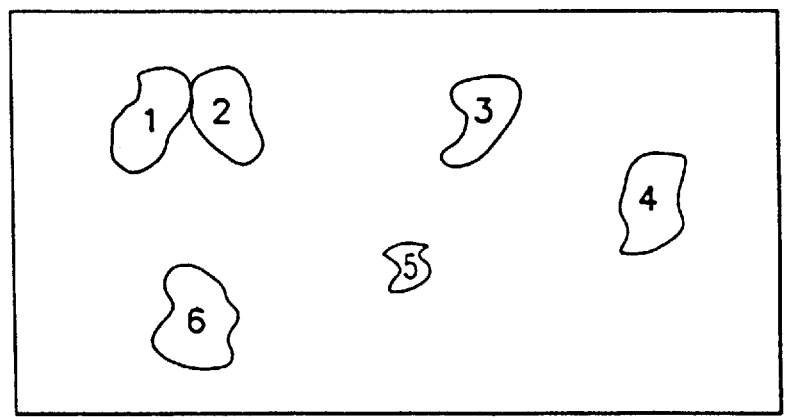

The field of view data, representing an image of the field of view of the microscope imaging apparatus, is processed individually to identify objects of interest within the field of view. The result of the subject method for identifying objects of interest, i.e., cells in the case of a cervical Pap smear, is a mask that identifies the size, shape, and location within the field of view of the object of interest and a mask that provides a unique identification value to each object in the image. With reference to FIG. 2A, a field of view of a microscope is illustrated including several objects of interest labeled 200, 202, 204, and 206. FIG. 2B illustrates the mask that will be developed for identifying the size, shape, and location of the objects of interest illustrated in FIG. 2A. FIG. 2C illustrates the mask that will be generated to provide the identification value to the objects of interest illustrated in FIG. 2A. It will be appreciated by those skilled in the art that when used for cervical Pap smear analysis, in addition to other cell analysis, the subject invention will provide the mask illustrated in FIGS. 2B and 2C for both the nucleus and cytoplasm of each cell contained within the field of view of the microscope. Further, it will be apparent to those skilled in the art that the illustration provided in FIGS. 2B and 2C are representations of data generated in accordance with the subject invention, and are not necessarily provided as the output of the method. The representations are provided here only to help in the description of the invention.

To identify the objects of interest and provide the mask illustrated in FIGS. 2B and 2C, the subject method first enhances the contrast between the objects of interest and the background, step 102. This enhancement is provided to increase the differential between data representing the edge of an object and data representing the background. Thereafter, each object in the field of view is subjected to a threshold test to determine whether the brightness of the object lies within a predetermined range of brightness expected for objects of interest. Since the field of view may contain artifacts in addition to objects of interest, it is desirable to not only identify the size, shape, and location of the objects of interest, but to also eliminate from further analysis any artifacts, e.g., hair, dirt, dust, etc., that may inadvertently appear in the field of view. To this end, a range of predetermined values are provided for several characteristics of the objects of interest wherein the objects of interest are expected to lie within the range of values provided. The characteristics that are examined are brightness, size, and shape. It will be apparent, however, to those skilled in the art, that if the subject method is applied to other types of image analysis systems, other characteristics may be selected to identify various other objects of interest.

After performing the threshold test of step 104, the objects of interest have been identified. The next step, therefore, is to refine the image of the objects of interest and to produce the mask illustrated in FIGS. 2B and 2C, step 106.

Figure 3:
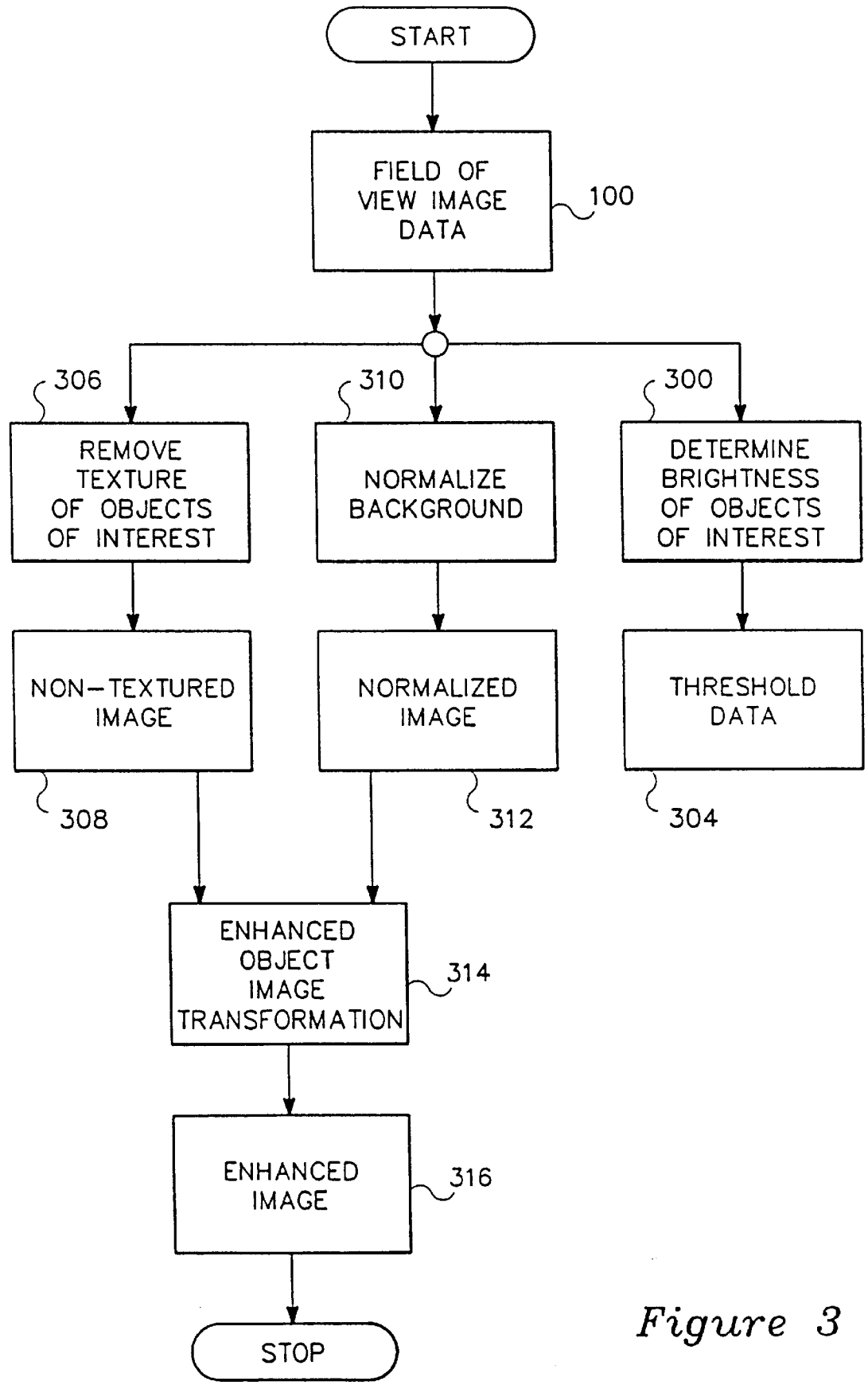
FIG. 3 is a method flow diagram illustrating substeps for executing step 102 of FIG. 1.

A more detailed decision flow diagram illustrating the method for preforming the contrast enhancement of step 102 is provided in FIG. 3. The first step in enhancing the image is to determine selected parameters of the field of view data. In the embodiment of the invention illustrated in FIG. 3, the selected parameters are the brightness of the nucleus, cytoplasm, and background, step 300. Those skilled in the art will appreciate that the image analysis system may, for various reasons, have variations in brightness from field of view to field of view. The most obvious contributor to brightness variation being the brightness in the illumination system, or light provided to the slide, prior to taking the field of view image data. However, other factors can contribute to variation in brightness from one field of view to the next. Accordingly, the determination of step 300 is made to effectively scale the brightness of the subject field of view.

Figure 4A:
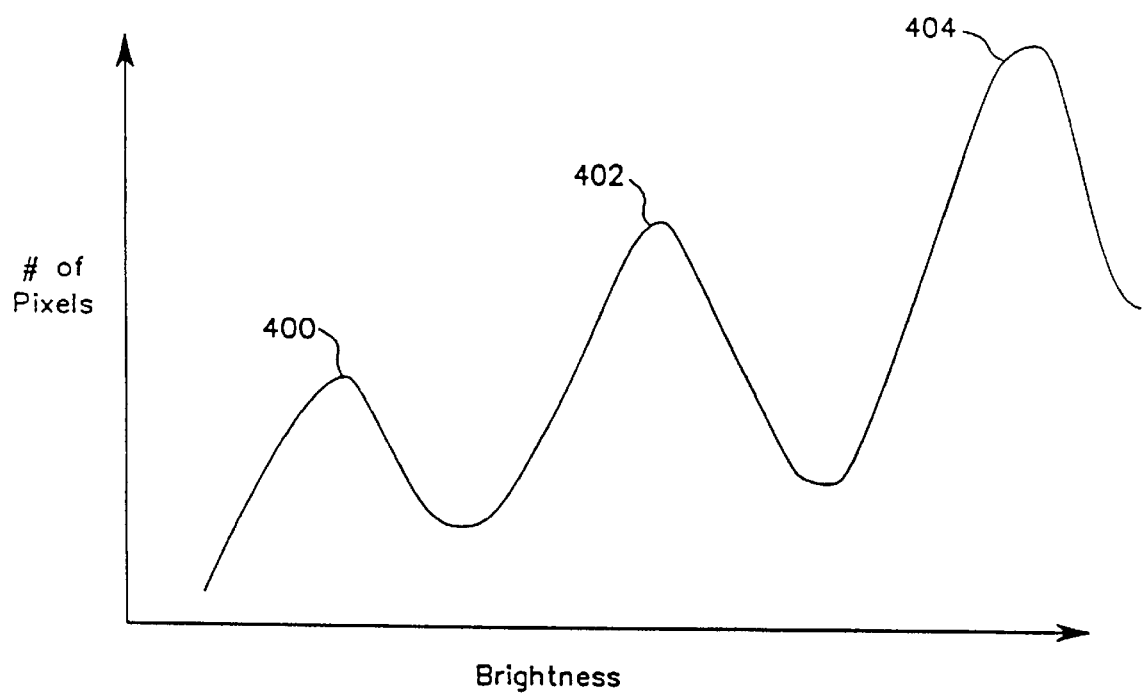
FIG. 4A is a graph illustrating an ideal distribution of pixel brightness for a slide used in combination with the subject invention.

The brightness determination of step 300 may be performed by using a histogram function to determine how many pixels within the grayscale field of view have a certain brightness. The results of the histogram may be graphed as illustrated in FIG. 4A. Ideally, the result of the histogram will be a curve having three peaks, wherein the brightest peak 404 is indicative of the number of pixels presenting the background of the field of view. The medium brightness peak 402 is indicative of the number of pixels representing the cytoplasm of the cell of interest, and the darkest peak 400 represents the number of pixels representing the nucleus of the cell.

Figure 4B:
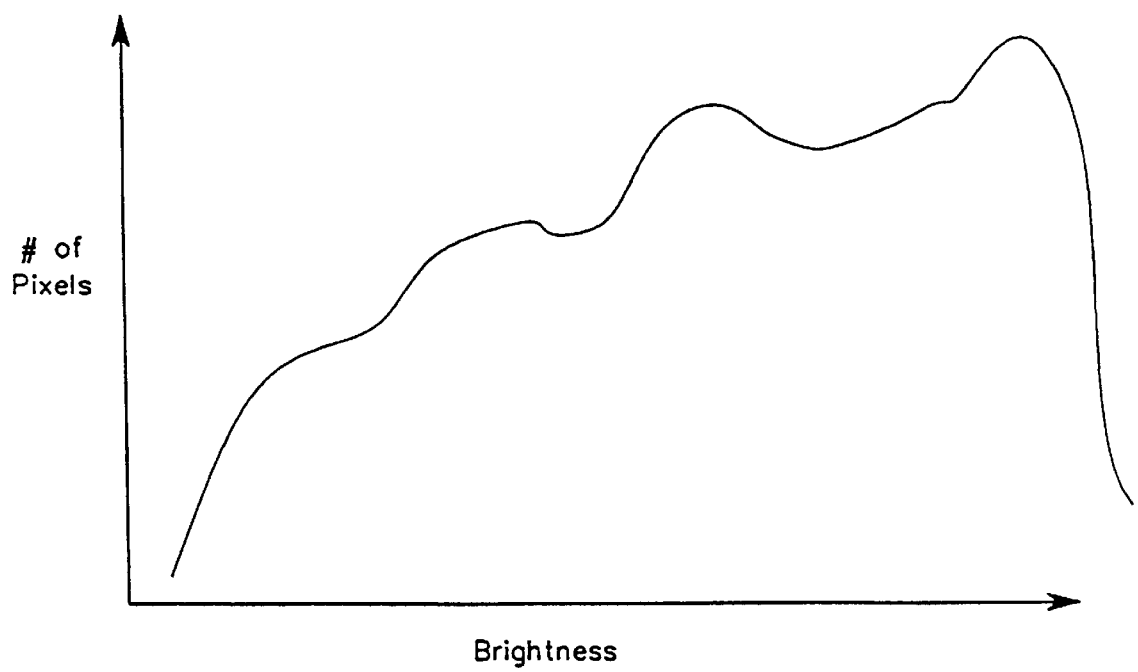
FIG. 4B is a graph of a distorted histogram wherein the peaks are virtually indistinguishable from the valleys and wherein the brightness at which the peak occurs is indeterminate.

However, since the subject method is intended for use without any special preparation of the specimen, cells may be provided in overlapping fashion or in clumps. These cells will tend to distort the results of the histogram, thereby deviating the histogram from the ideal illustrated in FIG. 4A. Such a distorted histogram is illustrated in FIG. 4B wherein the peaks are virtually indistinguishable from the valleys and wherein the brightness at which the peak occurs is indeterminate. To reduce the impact of overlapping cells on the parameter determination of step 300, morphological functions such as repeated dilation and erosion may be performed to remove overlapped objects from the field of view. The morphological functions of dilation and erosion are well known to those skilled in the art and need not be discussed in detail here.

Figure 5:
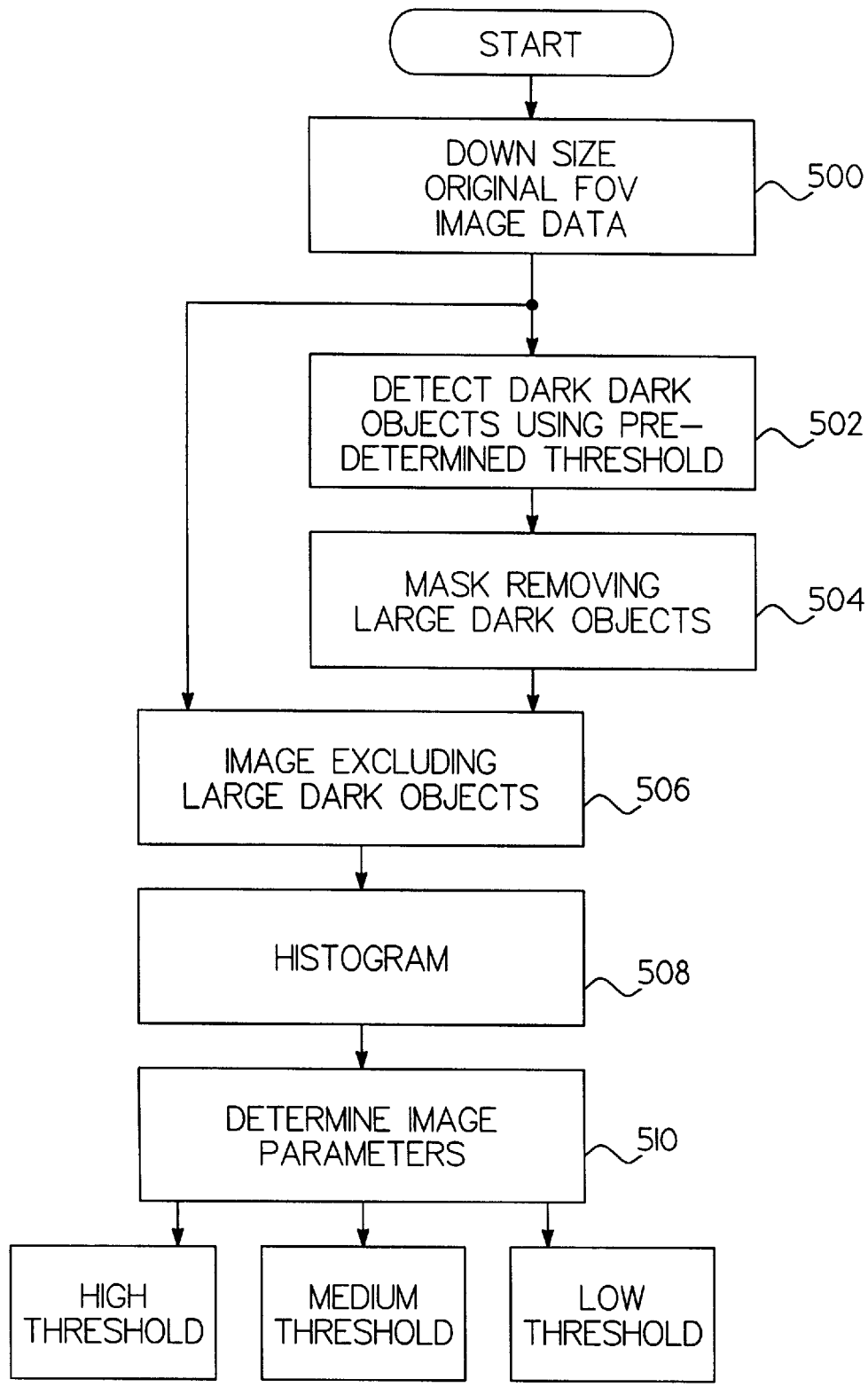
FIG. 5 is a method flow diagram illustrating steps used to determine the brightness distribution of pixels for a particular field of view.

Referring to FIG. 5, a method is provided for determining the brightness of objects of interest and providing the threshold data of steps 300 and 304. Therein, the original image is first downsized, step 500. Downsizing of the original image is performed to save time in the parameter estimation stage. It is noted that detail of the size and shape of the original field of view image are not necessary for accurate determination of the threshold data. Downsizing may readily be performed by methods known in the art. A particularly novel method for downsizing the original image is shown and described in the above referenced U.S. Patent entitled Method and Apparatus for Rapidly Processing Data Sequences, by Richard S. Johnston et al.

After downsizing of the original image, dark objects are detected using a predetermined threshold. This is performed by eliminating all field of view image data that is not equal to or above the predetermined threshold, step 502. Thereafter, the large objects are removed from the image generated in step 502. Removal of the large objects can be obtained using an opening residue operation. As is known in the art, an opening residue is simply a morphological opening to produce an opened image followed by a difference operation to combine the opened image with the original image. Thereafter, the downsized image is combined with the image created in step 504 to exclude the large dark objects detected by the image of step 504 from the downsized image of step 500, step 506.

As discussed above by reference to FIGS. 4A and 4B, overlapped and closely packed cells will distort any distinction between the brightness of the nucleus, the cytoplasm, and the background of the field of view, thereby making the parameter determination extremely difficult, if not impossible. Steps 502 and 504 are therefore intended to remove large dark objects from the image data used for parameter determination, thereby isolating representative objects of interest. Those skilled in the art will appreciate that overlapping cells will be dark and distinguished from the dark nucleus by their size. Accordingly, steps 502 and 504 are intended to remove objects having a darkness similar to that expected for the nucleus and having a size much greater than that expected for the nucleus. It will be apparent to those skilled in the art that in other applications other criteria could be selected to remove objects that distort the parameters and to isolate objects representative of the parameters being measured.

After the large dark objects are removed from the downsized image, step 506, a histogram is performed, step 508, and the image brightness parameters determined, step 510. In the present embodiment of the invention, used to identify cells in a cervical Pap smear, the results of the image determination, step 510, is a high threshold representing background, a medium threshold representing cytoplasm, and a low threshold representing the nucleus, as also illustrated in FIG. 4A.

The results of the parameter determination of step 300 is threshold data providing data indicative of the expected threshold of the nucleus, cytoplasm, and background of a particular field of view of a particular specimen, step 304. Those skilled in the art will appreciate that the threshold data must be determined uniquely for each field of view since the variations in the image analysis system discussed above will cause the parameters to change from field of view to field of view. Further, although the parameters of the embodiment discussed herein are brightness of the objects of interest, other parameters could be selected and determined in various other applications.

As mentioned above, the results of the subject method are to create a mask that identifies the size, shape, and location of the objects of interest, and to provide an ID value to the objects of interest, as illustrated in FIGS. 2B and 2C. However, the objects of interest may appear to have texture, i.e., brightness discontinuities, that may detract from the ability to produce a mask. Accordingly, it is desirable to remove the texture of the objects of interest, step 306. With particular reference to the image of cells of a cervical Pap smear specimen, it is desirable to remove the texture of the nucleus of any cells appearing in the field of view image. The texture removal may be accomplished on the original image by a grayscale morphological opening, as is known in the art. After the opening, the boundary of the objects of interest are recovered by conditional dilation. Thereafter, the remainder of the images are recovered to provide a non-textured image, step 308.

The background is then normalized to decrease the difference in contrast between the background and the objects of interest, step 310. This step is particularly useful for imaging of cells, or other objects of interest, where the object of interest includes two portions having different levels of brightness, i.e., the nucleus and cytoplasm in the case of cell imaging. The result of the background normalization is to provide a normalized image, step 312.

The normalized image provided from step 312 and the non-textured image provided by step 308 are combined in step 314 to provide the enhanced image that is part of the result of step 102. The enhanced object image transformation of step 314 is performed by transforming the image to eliminate the effect of intensity variation due to nonuniform staining of the specimen. As is known in the art, a Pap smear is performed by staining a specimen to chemically enhance the difference in the transmissivity between portions of the specimen, i.e., the nucleus, the cytoplasm, and the background. However, since the staining can be nonuniform over the specimen, variations in grayscale intensity of the field of view image may result. The image transformation of step 314 is performed by using Gaussian averaging techniques to mitigate against this nonuniformity. Particularly, the original image is filtered in a binomial filter. The non-textured image is then subtracted from the filtered image to provide the enhanced image, step 316.

Accordingly, as illustrated in FIG. 3, the result of the contrast enhancement discussed above by reference to step 102, FIG. 1, is to provide threshold data illustrating the grayscale intensity of various portions of the object of interest and the background, and to provide an enhanced image wherein the contrast between the background and the object of interest is enhanced.

Returning to FIG. 1, the threshold test to identify objects of interest, step 104, is performed on the enhanced image (produced from step 316, FIG. 3) using the threshold data (produced from the method of FIG. 5) to produce a binary image. The threshold test is generally one to compare each data word from each pixel of the field of view image data with a predetermined threshold value, and to identify as an object of interest any object having an intensity greater than the predetermined value. However, a particularly novel feature of the subject invention is that the value of the threshold is varied for each pixel. Stated another way, a threshold image is generated wherein the threshold image includes a threshold intensity value associated with each pixel of the field of view. The threshold test is thus performed by comparing the threshold intensity value associated with a particular pixel with the data word from that pixel. As is known in the art, if the data word is greater than or equal to the threshold intensity value, then the respective pixel of the binary image is assigned a "one" to indicate the presence of an object. Conversely, if the data word is less than or equal to the threshold intensity value, then the respective pixel of the binary image is assigned a "zero" to indicate the absence of an object.

Figure 6:
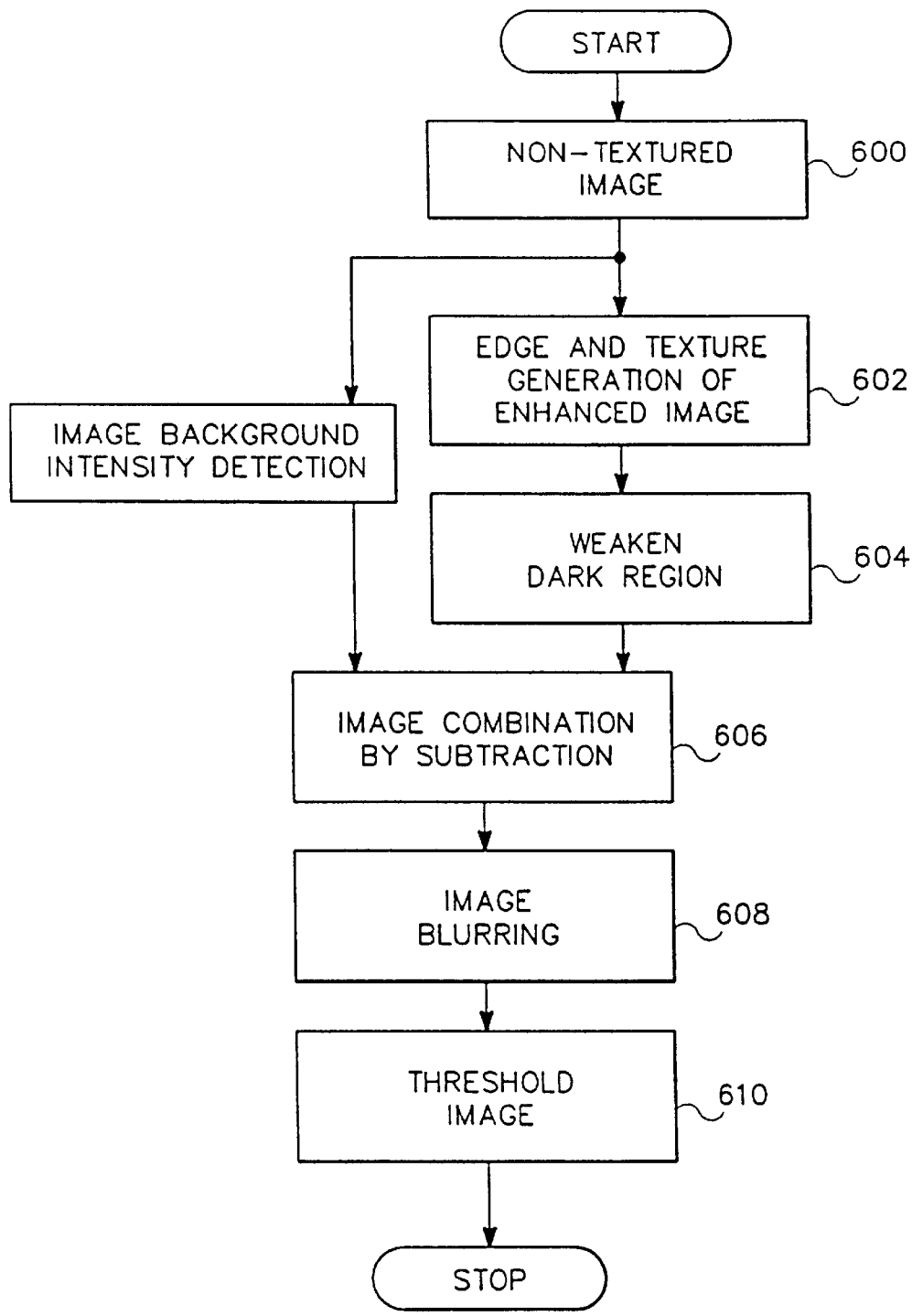
FIG. 6 is a method flow diagram illustrating steps used to create a threshold image in accordance with the subject invention.

With reference to FIG. 6, a method for generating a threshold image will be discussed. The threshold image is generated from the non-textured image and the enhanced image. The background of the non-textured image (see step 308 of FIG. 3) is removed, step 600. Thereafter, the edge and texture of the enhanced image is generated, step 602, and the dark region weakened, step 604. The edge image is determined by a morphological dilation residue operation, and the texture image is derived by the difference of the non-textured image and the original image. The images resulting from step 600 and 604 are combined, step 606, and the combined image blurred, step 608, to produce the threshold image, step 610.

As mentioned above, the threshold image is combined with the original image to identify the objects of interest. The threshold image generated above, as described by reference to FIG. 6, may be used by itself with the original image to identify objects of interest, however, in a presently preferred embodiment of the present invention, the threshold image is combined with the enhanced image to identify objects of interest. Additionally, as will be described in more detail below, the threshold image is combined with two predetermined offset values to generate three threshold images. A first predetermined offset is subtracted from each grayscale pixel value of the original threshold image to create a low threshold image, and a second predetermined value is added to each grayscale pixel value of the threshold image to create a high threshold image. The low threshold image, high threshold image, and original threshold image are each separately combined with the enhanced image to provide three binary threshold images.

It will be apparent to those skilled in the art that each of the images discussed hereinabove have been grayscale images, i.e., images wherein each pixel may have a range of values representing a variety of intensities. After the threshold images are combined with the enhanced image, as discussed above, the result is a binary image, i.e., an image wherein each pixel represents either the presence or absence of an object. Since the result of the subject method is to provide a mask, those skilled in the art will appreciate that the binary images produced by combining the threshold images with the enhanced image represents the mask that identifies the shape, size, and position of each object of interest within the field of view.

Still further, those skilled in the art will appreciate that a combination of the original threshold image with the enhanced image will provide a mask that identifies the size, shape, and position, of objects of interest wherein the mask is suitable for most applications. However, in the present application of the subject method, it is desirable to perform further data processing of the field of view image data to ensure that all objects of interest have been properly identified and are represented in the mask. Accordingly, the three binary threshold images produced as a result of step 104 (FIG. 1), as discussed above, are refined, step 106, as will be discussed in more detail below.

Generally, refinement of the binary threshold images begins with the binary threshold image produced by combining the original threshold image with the enhanced image. Data processing is performed to determine whether any artifacts, or non-nucleus, have been identified. The result of these tests are to generate what represents a very close approximation of the desired mask. Thereafter, all objects identified in the high threshold binary image are added into the best approximation mask created above. Lastly, further data processing is performed to determine whether any additional objects of interest are identified in the low threshold binary image that have not yet been incorporated into the mask and, if so, these objects are also incorporated into the mask.

Figure 7A:
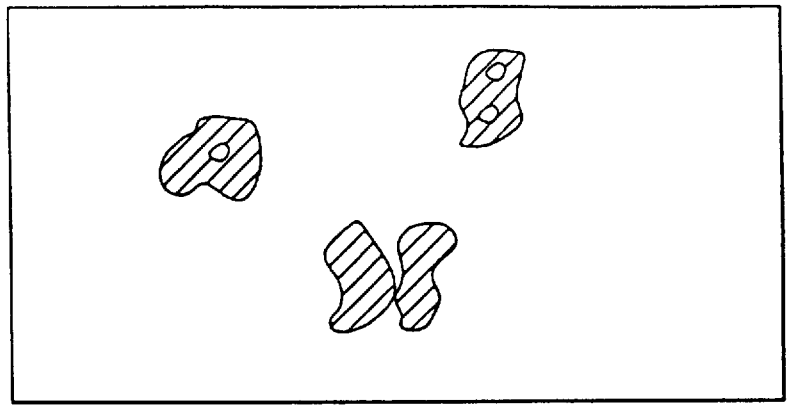
FIGS. 7A and 7B are diagrams illustrating a portion of the method for refining objects of interest in accordance with the subject invention.
Figure 7B:
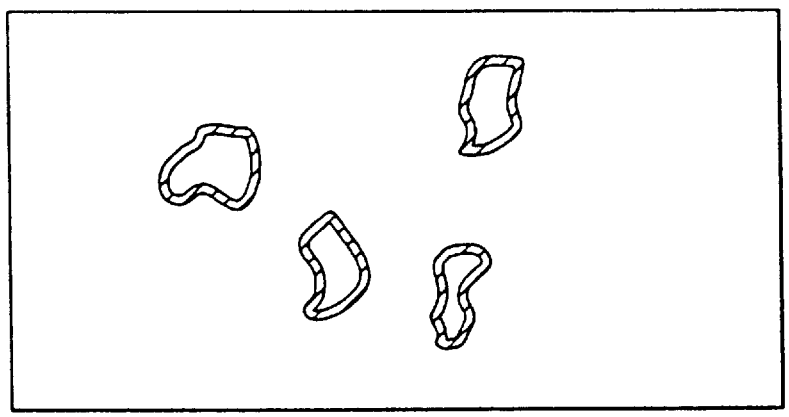
Figure 8:
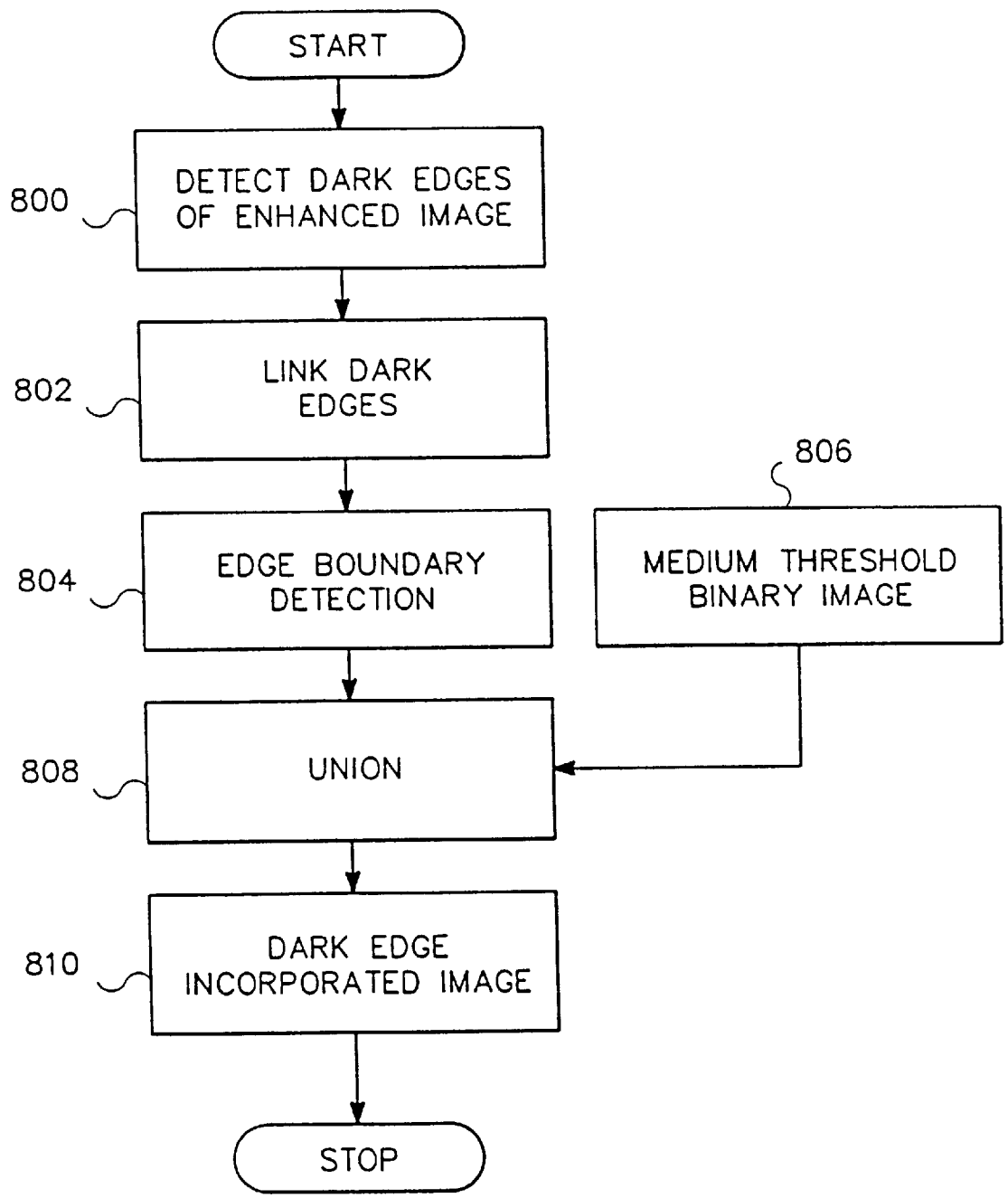
FIG. 8 is a method flow diagram illustrating steps for refining the objects of interest in accordance with the subject invention.

To refine the medium threshold binary image, the mask is operated upon to fill any holes. For example, the binary mask that should appear as indicated in FIG. 2B may have holes within objects of interest, as shown in FIG. 7A. The method of FIG. 8 is performed to refine the mask of FIG. 7A to eliminate any holes and provide a mask as illustrated in FIG. 2B. Initially, the dark edges of the objects of interest are identified by morphological erosion residue operations, as illustrated by the intermediate mask of FIG. 7B. To perform the dark edge incorporation, the dark edges of the enhanced image are detected. Dark edge detection in step 800 may be performed simply by determining where there exists a variation between a pixel and a neighboring pixel. The dark edge is identified as the pixel representing an object of interest. Next, the dark edges are linked using a small morphological closing and subsequent opening to fill in holes in the dark edge, step 802. Thereafter, the boundary of the edge is detected in step 804 and identified as the true dark edge mask, as illustrated in FIG. 7B. The medium threshold binary image 806 is then combined in a set union 808 with the image created by step 804 to create a dark edge incorporated image, step 810.

Figure 9:
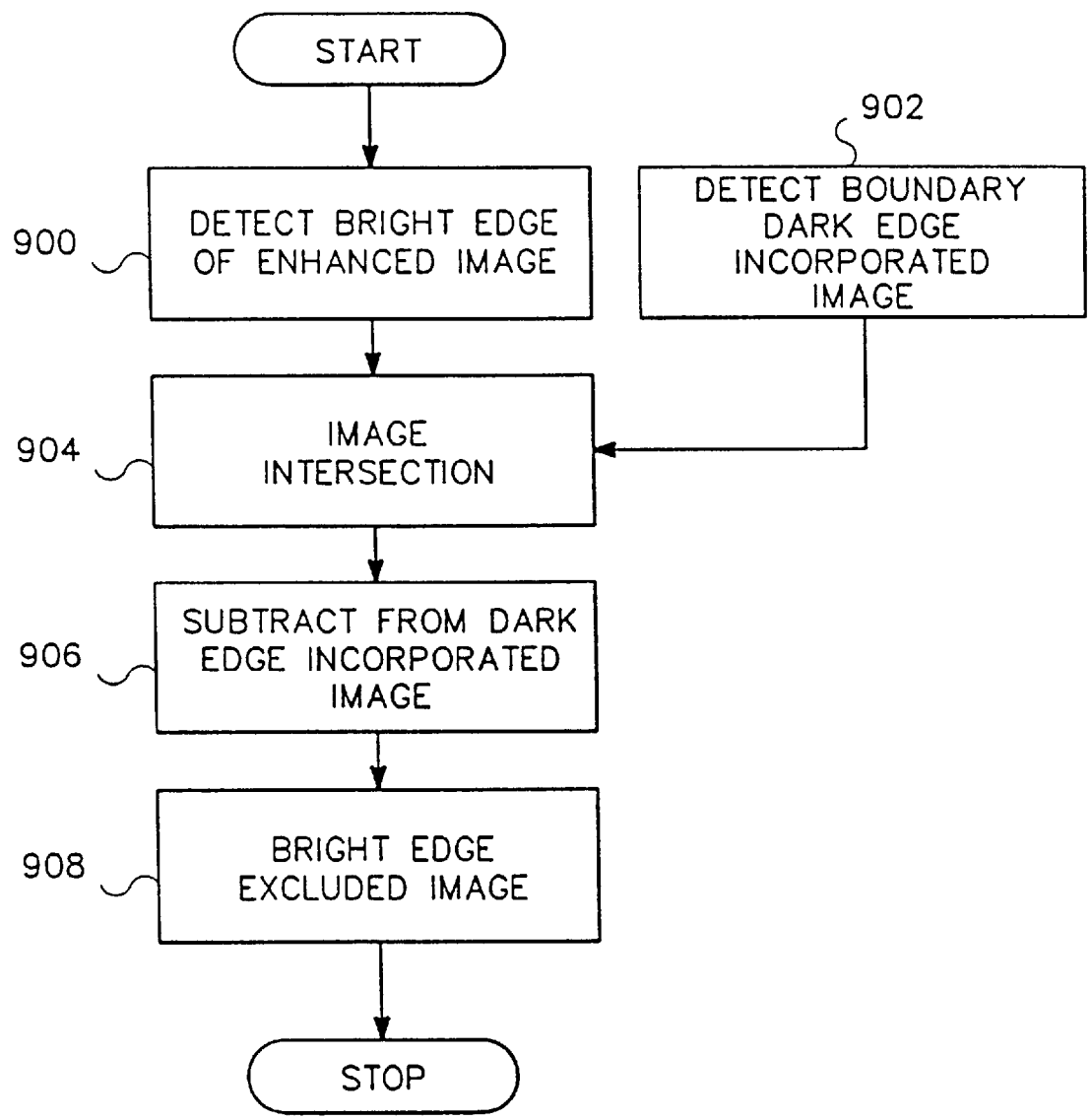
FIG. 9 is a method flow diagram illustrating steps for refining the objects of interest in accordance with the subject invention.

In similar fashion, the bright edges of the original image are then excluded from the medium threshold binary image. To this end, the bright edges of the enhanced image are detected, step 900, as illustrated in FIG. 9. This is performed in a manner similar to the dark edge detection of step 800, discussed above, except that the edges of the pixels representing the absence of an object are identified as the bright edge. The boundary of the dark edge incorporated image created in step 810, above, is then detected, and the results of step 900 and 902 combine in a set intersection operation. The results of step 904 are then subtracted from the dark edge incorporated image, step 906, to create a bright edge excluded image, step 908. The medium threshold binary image is now represented by the bright edge excluded image.

Figure 10A:
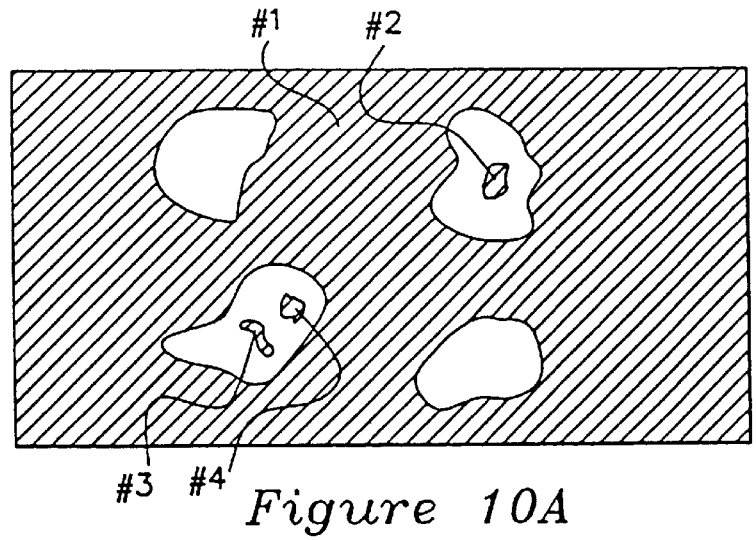
FIGS. 10A, 10B, and 10C are diagrams illustrating a novel method for eliminating holes in the objects of interest in accordance with the subject invention.
Figure 10B:
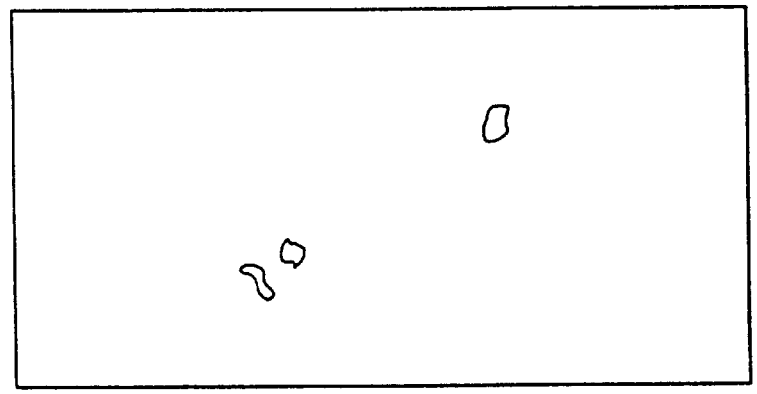

The objects of the bright edge excluded image are completed by filling any holes that may remain. Advantageously, the subject method is capable of filling holes without connecting close objects. To complete the refinement of the medium threshold binary image, the bright edge excluded image of step 908 is inverted to provide an image, as illustrated in FIG. 10A. Next, the objects of FIG. 10A are detected and labeled by a connected components labeling procedure. Objects are then identified that are larger than a predetermined size, and these objects are excluded from the image to provide an image as illustrated in FIG. 10B. The image thus created is then added to the original image to provide the completed medium threshold binary mask. It will be apparent to those skilled in the art that the predetermined size for excluding objects from the mask of FIG. 10A is selected to be larger than the expected size of objects of interest.

Figure 10C:
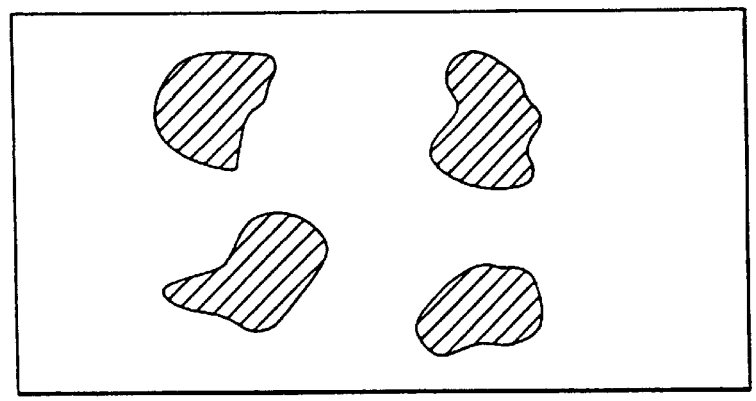

To further complete the medium threshold binary image, data processing is performed to separate objects that may not have been separated using the bright edge detection technique discussed above. To perform the object separation, the objects of the mask created in FIG. 10C are eroded by a first predetermined amount and then dilated by a second predetermined amount wherein the amount of erosion exceeds the amount of dilation, so that the objects after dilation are smaller than they were before erosion. Thus, the connected objects are separated. A morphological closing residue operation is then applied to determine the separation boundary. The separation boundary is then subtracted from the hole-filled image to create the overlap object separated binary image.

To ensure that no objects have been lost due to the above-noted separation, the overlap object separated image is dilated to generate an object mask. Small objects not included in the object mask are combined in a set union with the object separation image to provide an object recovered image.

Lastly, the high threshold binary image and the low threshold binary image are combined with the object recovered image, i.e., the completed medium threshold binary image, to create the final mask. To this end, all objects identified in the high threshold image are added to the completed medium threshold image using a set union operation. The resulting mask is then eroded by a small amount and dilated by a large amount, so that all significant objects that are identified and their surrounding areas are included in a protection mask. In a preferred embodiment of implementation, the erosion is applied using a 3 by 3 kernel and the dilation is performed using a 27 by 27 kernel. The resulting mask is then combined with the low threshold mask so that any objects identified in the low threshold mask in an area not in close proximity to objects appearing in the completed medium threshold mask are added to the image. These objects are then added to the completed medium threshold image to create the finished mask. A connected components labeling procedure is applied to the finished mask to assign a unique label to each connected object.

Figure 11A:
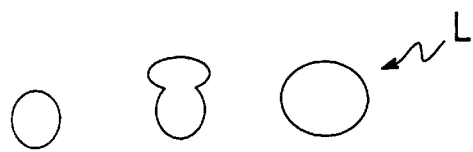
FIGS. 11A through 11H are diagrams illustrating the generation of a finished mask in accordance with one embodiment of the invention.
Figure 11E:
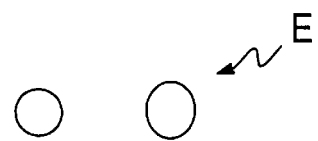
Figure 11B:
Figure 11F:
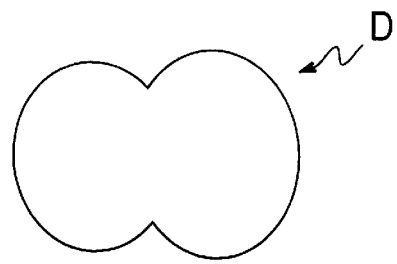
Figure 11C:
Figure 11G:
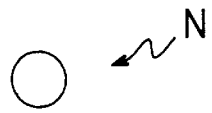
Figure 11D:
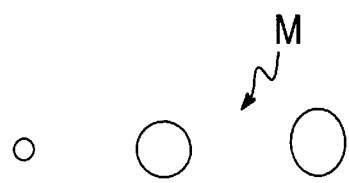
Figure 11H:
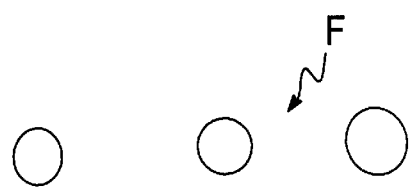

Referring now to FIGS. 11A through 11H, diagrams illustrating the generation of a finished mask in accordance with one embodiment of the invention are shown. FIG. 11A schematically shows one example of a low threshold binary image (L). FIG. 11B shows a recovered object image (R) and FIG. 11C shows a high threshold binary image (H). The medium threshold image (M) is generated by a set union of (R) and (H) as shown in FIG. 11D. The medium threshold image (M) is then eroded by a small amount (E) as illustrated in FIG. 11E. The eroded image (E) is then dilated by a large amount (D) as shown in FIG. 11F. An image mask (N) is created by excluding any area covered by the dilated image (D) from the low threshold binary image (L) as shown in FIG. 11G. FIG. 11H shows the finished mask (F) as generated by the set union of (N) and (M).

It will be appreciated that various modifications of the invention may be made without deviating from the spirit and scope of the invention. Accordingly, the invention is not limited except as by the appended claims.

What is claimed is:

1. A method for creating a mask to identify objects of interest wherein the objects of interest are contained in an image represented by an array of data words, said method comprising the steps of:

(a) processing the array of data representing the image to create a threshold image wherein the threshold image is an array of data words wherein each data word of the threshold image corresponds to a respective data word of the image;

(b) comparing each data word of the threshold image with its respective data word of the image to create a binary image wherein the binary image is an array of data words each corresponding to a respective data word of the image and wherein each data word of the binary image identifies whether the respective data word of the image was greater than the respective data word of the threshold image, the binary image representing the mask to identify the objects of interest;

(c) processing the binary image by a morphological operator;

(d) subtracting a predetermined offset from each data word of the threshold image to create an array of data representing a low threshold image;

(e) comparing each data word of the low threshold image with its respective data word of the image to create a low threshold binary image wherein the low threshold binary image is an array of data words each corresponding to a respective data word of the image and wherein each data word of the low threshold binary image identifies whether the respective data word of the image was greater than the respective data word of the low threshold image; and (f) adding objects identified by the low threshold binary image to the binary image.

2. The method of claim 1 wherein the morphological operator performs a morphological opening.

3. The method of claim 1 wherein the morphological operator performs a dilation.

4. The method of claim 1 wherein the morphological operator performs an erosion.

5. The method of claim 1 wherein the morphological operator performs a morphological dilation residue operation.

6. The method of claim 1 wherein the morphological operator performs an erosion residue operation.

7. The method of claim 1 wherein the morphological operator performs a small morphological closing and subsequent opening operation.

8. The method of claim 1 wherein the morphological operator performs a morphological closing residue operation.

9. A method for creating a mask to identify objects of interest wherein the objects of interest are contained in an image represented by an array of data words, said method comprising the steps of:

(a) processing the array of data representing the image to create a threshold image wherein the threshold image is an array of data words wherein each data word of the threshold image corresponds to a respective data word of the image;

(b) subtracting a predetermined offset from each data word of the threshold image to create an array of data representing a low threshold image; and (c) comparing each data word of the low threshold image with its respective data word of the image to create a low threshold binary image wherein the low threshold binary image is an array of data words each corresponding to a respective data word of the image and wherein each data word of the low threshold binary image identifies whether the respective data word of the image was greater than the respective data word of the low threshold image.

* * * * *